(12) United States Patent
Hills et al.

(10) Patent No.: US 6,482,391 B1
(45) Date of Patent: Nov. 19, 2002

(54) MEDICAMENTS FOR ASTHMA TREATMENT

(75) Inventors: Brain Andrew Hills, Cleveland (AU); Derek Alan Woodcock, Berkshampstead (GB)

(73) Assignee: Britannia Pharmaceuticals Limited, Surrey (GB)

( * ) Notice: Subject to any disclaimer, the term of this patent is extended or adjusted under 35 U.S.C. 154(b) by 0 days.

(21) Appl. No.: 09/555,743

(22) PCT Filed: Nov. 26, 1998

(86) PCT No.: PCT/GB98/03543

§ 371 (c)(1),
(2), (4) Date: Aug. 10, 2000

(87) PCT Pub. No.: WO99/27920

PCT Pub. Date: Jun. 10, 1999

(30) Foreign Application Priority Data

Dec. 3, 1997 (GB) ............................................... 9725640
Dec. 24, 1997 (GB) ............................................... 9727276

(51) Int. Cl.[7] ............................. A61K 9/12; A61K 9/14; A61K 9/127
(52) U.S. Cl. ......................... 424/45; 424/450; 514/959; 514/958; 514/826
(58) Field of Search ................... 424/45, 450; 514/959, 514/958, 826

(56) References Cited

U.S. PATENT DOCUMENTS

| | | | | |
|---|---|---|---|---|
| 4,895,719 A | * | 1/1990 | Radhakrishnan et al. | ...... 424/45 |
| 5,234,953 A | * | 8/1993 | Crow et al. | .................. 514/573 |
| 5,306,483 A | * | 4/1994 | Mautone | ........................ 424/45 |
| 6,013,619 A | * | 6/2000 | Cochrane et al. | .............. 514/2 |

FOREIGN PATENT DOCUMENTS

| | | |
|---|---|---|
| DE | 3229179 | 2/1984 |
| EP | 0528034 | 2/1993 |
| EP | 0689848 | 3/1996 |
| JP | 58164513 | 9/1983 |
| WO | 9729738 | 8/1997 |

OTHER PUBLICATIONS

Sorkness et al., "A double–blind . . . asthma", J. Allergy Clin. Immunol. V.95, No. 1 Part 2, p. 352, 1995.

* cited by examiner

Primary Examiner—Jose' G. Dees
(74) Attorney, Agent, or Firm—Roylance, Abrams Berdo & Goodman

(57) ABSTRACT

A method and apparatus is disclosed for treating asthma and other respiratory conditions. A medicament comprising a surface active phospholipid (SAPL) is prepared in the form of a fine powder and administered to the lungs in a gas stream. A preferred SAPL is a solid blend of dipalmitoyl phosphatidyl choline (DPPC) and phosphatidyl glycerol (PG).

11 Claims, 1 Drawing Sheet

MEDICAMENTS FOR ASTHMA TREATMENT

This invention relates to artificial lung surfactants and their use in the treatment of asthma.

It has been estimated that asthma affects between 4 and 10 percent of the population causing distress and alarm to both sufferers and bystanders. Asthma attacks appear to be precipitated in many cases by a number of factors such as exercise or pollutants in the inspired air. Other agents such as pollen and airborne particles may predispose an asthma sufferer to an attack by sensitising the airways. This has led to the belief that effective treatment should include administration of drugs which reduce the sensitivity of asthma sufferers to allergens or which neutralise the allergic reaction.

The present invention is based on a different approach namely that the lungs and airways of non-asthnmatics may contain a natural protective barrier which prevents pollutants and other airborne triggers from reaching receptors whose irritation would then produce an acute attack. While not wishing to be bound by any fixed theory at this stage, studies have suggested that SAPL masks (covers) most of these receptors in normal lungs but this masking is deficient in asthmatics. The present invention is predictated on the belief that it is possible to restore normal masking by binding surface-active phospholipids (SAPL) to the tissue surface of the lungs. thereby reducing the number of receptors exposed to noxious stimuli and reducing hyper-responsiveness of the broncho-constrictor reflex common to all forms of asthma.

SAPL's are used clinically for the treatment of neonates with respiratory distress syndrome (RDS). In this role. it has been assumed that the SAPL functions by reducing the high surface tension of the air-water interface within the alveoli, thereby reducing the pressure needed to expand the lungs, see Milner, Archives of Diseases in Childhood 1993; 68–253. Thus, commercially available formulations of SAPL have been designed to spread rapidly over an air-aqueous interface, thereby reducing what is otherwise a very high surface tension of water.

Limited clinical studies have been carried out to determine the effect of commercial SAPL's marketed for treatment of RDS in neonates on asthmatic subjects, —see Kurashima et al. Jap. J. Allergol 1991; 40, 160. This paper reported some amelioration of bronchoconstriction in asthmatic adults using an SAPL obtained by extraction from bovine lungs. In another study on children, also using an SAPL obtained from bovine lungs, no significant changes in lung function or histamine response were found, —see Oetomo et al—American Journal of Respiratory and Critical Care Medicine 153; 1996, page 1148.

Our approach to the problem differs from these studies in that it involves the use of an anti-asthma medicament which is capable of binding (absorbing) to the tissue surface (epithelium) of the airways, thereby masking receptors against stimulation by noxious agents or sensitisation by allergenic stimuli. Although it is an advantage for the medicament employed in this invention to spread over the surfaces of the airways, once in place, one or more components of the composition will migrate across the mucous layer and deposit a thin hydrophobic lining on the tissue surface, and/or supplement the indigenous coating.

According to one of its aspects, the present invention comprises use of a surface active phospholipid (SAPL) composition in the preparation of a medicament for the treatment of asthma by administration of the medicament to the patient's airways and upper respiratory tract, said medicament comprising SAPL and containing a component capable of binding to the surface of lung tissue.

Figure 1:
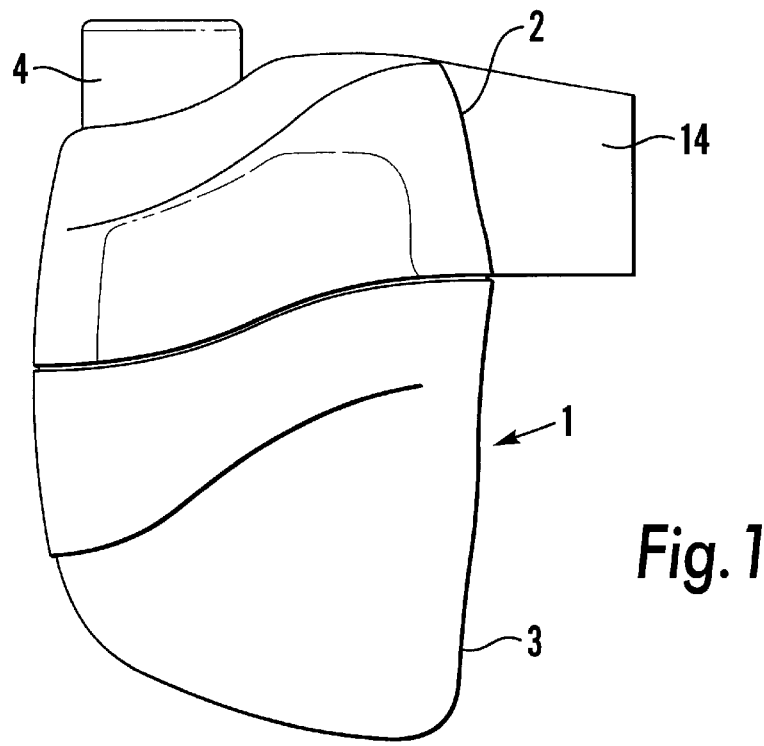
FIG. 1 Apparatus for administering the surface-active agent.

Examples of SAPL's which appear to be capable of forming a thin film or coating on surfaces of the lungs include diacyl phosphatidyl cholines (DAPC's ), e.g. dioleyl phosphatidyl choline (DOPC); distearyl phosphatidyl choline (DSPC) and dipalmitoyl phosphatidyl choline (DPPC). The SAPL is preferably administered as a dry powder. Another preferred component of the medicament is a spreading agent. Its function is to reduce the melting point of the DAPC so that it rapidly spreads as a thin film at normal body temperature. Suitable spreading agents include phosphatidyl glycerols (PG); phosphatidyl ethanolamines (PE); phosphatidyl serines (PS) and phosphatidyl inositols (PI). Another useful spreading agent is chlorestyl palmitate (CP). Alternatively, it is possible to reduce the melting temperature and hence improve the spreading characteristics of a DAPC by employing a DL mixture of the phospholipid. The above spreading agents, especially PG, are believed to enhance or potentiate the binding of the DAPC, especially the DPPC, to the epithelial surface.

Dipalmitoyl phosphatidylcholine (DPPC) is believed to be capable of binding to lung tissue and is, therefore, a preferred component of the SAPL. Phosphatidyl glycerol (PG) may function also in this way and is also a preferred component of the SAPL. PG has a further important function in medicaments employed in the present invention and this is its ability to cause the SAPL to form a very finely-divided, dry powder dispersion in air. Such dispersions may have particle sizes in the range of 0.5 to 20 $\mu$m, preferably 0.5 to 5 $\mu$m and more preferably 0.5 to 2 $\mu$m. Typically, the median particle diameter is about 1.2 $\mu$m. Finely divided dry powders of this kind (which may be described as filmed powders) are adsorbed onto the surfaces of lung tissue, i.e. bound to the epithelium, Preferably, the SAPL compositions employed in the present invention are blends of dipalmitoyl phosphatidylcholine (DPPC) and PG.

The medicament should generally be essentially free from animal protein in order to avoid the danger of patient sensitivity to animal proteins and pyrogens. Also, surfactants which are derived from animal proteins are not available in a finely-divided particle form which can be dispersed in a carrier gas stream.

DPPC can be prepared synthetically by the use of acyl chlorides using the method of Baer & Bachrea—Can. J. Of Biochem. Physiol 1959; 37, page 953 and is available commercially from Sigma (London) Ltd. The PG may be prepared from egg phosphatidylcholine by the methods of Comfurions et al and Dawson, Biochem. Biophys Acta 1977; 488; pages 36–42 and Biochem J. 1947; 192; pages 205–210. When co-precipitated with DPPC from a common solvent such as chloroform, PG forms with DPPC a fine powder which spreads rapidly over the surfaces of the airways and lungs. At a weight ratio of DPPC:PG of about 7:3, the mixture spreads rapidly at a temperature of about 35° C. and above. Additional or lesser quantities of PG can be incorporated into the composition and finely-divided compositions obtained. In general, DPPC and PG may be present in a weight ratio of from 9:1 to 1:9. Other DAPC's and other spreading agents may be used in similar proportions. Compositions employed in currently tested formulations have been in the weight ratio of from about 6:4 to 8:2. A SAPL suitable for use in accordance with the invention is obtainable from Britannia Pharmaceutical Ltd., 41–51 Brighton Road, Redhill, Surrey, under the trade mark 'Alec'.

Because we are concerned in the present invention to achieve a long term adsorption of the medicament on the lung surface, it is highly desirable that the SAPL (or its active component) should not break down in the environment of the lungs. One of the factors which will reduce the life of a lining or coating will be the presence of enzymes, such as phospholipase A, capable of digesting DPPC and/or PG. Such enzymes only attack the laevo rotatory (L) form, which constitutes the naturally occurring form. Therefore, the medicament should preferably contain the dextrorotatory (D) form or at least comprise a racemic mixture, which is obtained by synthetic routes.

The medicaments employed in the present invention are generally finely-divided dry powders having a particle size distribution which is small enough to be introduced into the airways and, preferably, deeply into the lungs in a gas stream from a dispersion device. Generally, medicaments are preferred in which the particle size distribution is such that a major proportion are between 0.5 and 2 micrometers. Suitable dispersion devices may employ a propellant such as a halocarbon to form the gas stream and may include a tapered discharge nozzle baffle or a venturi to accelerate particles through a discharge nozzle, and to remove oversized particles. Suitable halocarbons include hydrofluorocarbons, hydrofluorochlorocarbons and fluorochlorocarbons having a low boiling point, such as those marketed under the trade mark "Freon". The medicament may be packaged with a propellant in a pressurised aerosol container within the inhaler. Other inhalers have an impeller which mixes the powder into an air stream and delivers the powder-laden air into the patient's airways—see, e.g. U.S. Pat. No. 5,577,497.

The invention also includes a dispersion device for administering a medicament useful in the treatment of asthma which comprises a sterile cartridge containing finely-divided particles of an essentially protein-free mixture of DPPC and PG, and means for introducing said particles into a gas stream as the patient inhales, said particles including a majority having particle sizes within the range of 0.5 to 2 μm.

A preferred method and apparatus for administering the medicament involves dispersing the powdered medicament in a propellant gas stream For example, a pressurised canister of a liquefied gas may be connected to a vial containing the medicament. By releasing controlled amounts of gas from the canister into the vial, increments of the medicaments are ejected from the vial as a cloud of powder and may be inhaled by the user.

A typical design of the dispenser is shown in the accompanying drawings, in which:

FIG. 1 is a side elevation of the dispenser; and

Figure 2:
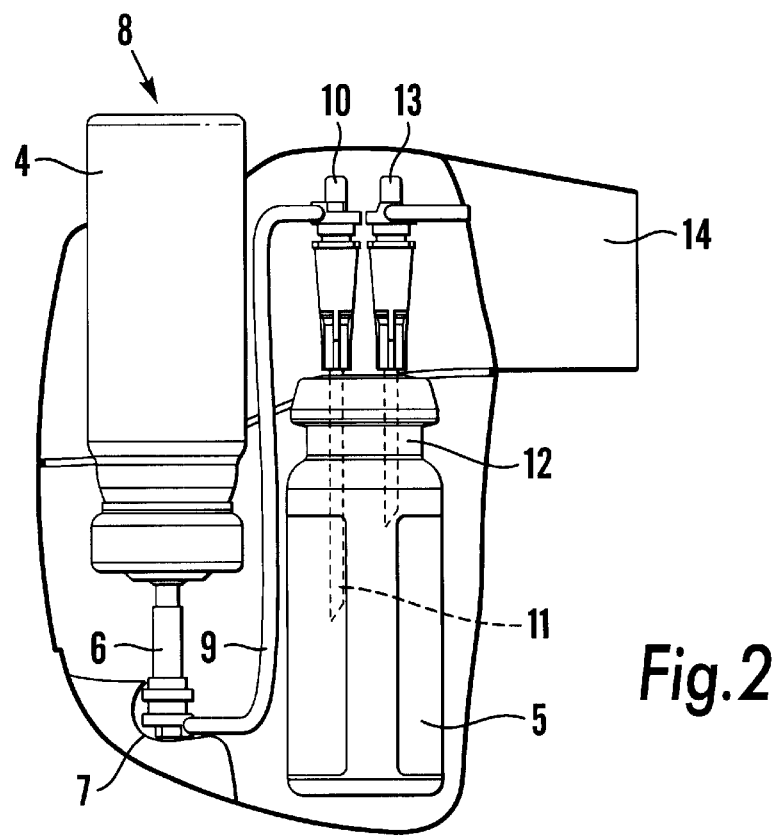
FIG. 2 Interior view of device as shown in FIG. 1.

FIG. 2 is a similar view, but shows its interior.

In the drawings, a casing (1) is formed from two plastic mouldings (2 & 3) which snap together to form a container for a pressurised canister (4) and a vial (5). Canister (4) contains a low boiling liquid, preferably a hydrofluorocarbon such as HFA-134a or HFC-227, under sufficient pressure to maintain the propellant liquid at normal room temperature. Vial (5) contains the powdered medicament, such as "Alec". Canister (4) has a release valve (6) which is received in a recess (7) so that finger pressure on the inverted end (8) of the canister will cause propellant to be released into a tube (9). Tube (9) is typically a hard plastics, e.g. pvc or polypropylene, tube of about 2~3 mm outside diameter and about 0.5 to 2 mm inside diameter. Tube (9) connects valve (6) with a fitting (10) and thence to a tube or needle (11) which extends into the vial (5). Vial (5) may be closed with a rubber seal which is penetrated by the tube or needle (11) and self-seals around the tube or needle. A second needle or tube (12) extends part way into the vial through the rubber seal in the neck of the vial and connects with a fitting (13). Fitting (13) discharges into a mouthpiece (14) which is a comfortable shape for the user to place in the mouth. When the patient is in need of medication, he places the mouthpiece (14) into his mouth and breaths and simultaneously depresses the canister (4). This causes a cloud of medicament to be dispensed into the patient's airways. Fittings (10) and (13) may be valves. Valves (10) may be set to permit measured quantities of propellant to enter the vial. Similarly, valve (13) may be set to release when the pressure in the vial reaches a predetermined level. It will be appreciated that the dispenser can be used one-handed in an analogous manner to a conventional nebulizer.

In addition to the powdered SAPL, the vial may incorporate other known pulmonary or respiratory medicaments such as 'Salbutamol', 'Beclomethasone. Corticosteroids, or other asthma drugs. It is, however, preferred to package the conventional asthma drug in the propellant canister or in a capsule interposed between the propellant container and the vial containing the SAPL. In this way, the lungs and airways receive a cloud of SAPL and an aerosol of the conventional drug sequentially or simultaneously. This combined therapy gives both quick relief and lasting protection as the film of SAPL spreads over the lung tissue. Instead of packaging the SAPL in a multi-use vial, it may be contained in a capsule, which may be a single use quantity, between the outlet from the propellant canister and the mouthpiece.

While the present invention has been described with particular reference to the treatment of human patients for asthma, it is possible that the invention may also be applicable to the treatment of other pulmonary diseases or conditions such as rhinnitis.

The medicament of the present invention may also be employed in the treatment of pulmonary conditions in other mammals. An example is reactive airway disease in horses.

What is claimed is:

1. A method of treating asthma comprising, administering an essentially animal protein-free surface active phospholipid (SAPL) composition to airways of an asthma patient, wherein said composition comprises an SAPL and a component that binds to the surface of lung tissue, and is a finely divided solid form wherein the major proportion of the particles in said composition are between 0.5 and 20 μm such that said composition can be introduced into the airways by carriage in a gas stream.

2. The method of claim 1, wherein the gas stream comprises a halocarbon which is gaseous at ambient temperatures.

3. The method of claim 2, wherein the halocarbon is tetrafluoroethane or heptafluoropropane.

4. The method of claim 1, wherein the component that binds to lung tissue comprises phosphatidyl glycerol (PG).

5. The method of claim 1, wherein the SAPL composition comprises a blend of dipalmitoyl phosphatidylcholine (DPPC) and PG.

6. The method of claim 5, wherein the PG is present in an amount sufficient to lower the temperature at which DPPC will spread spontaneously over a surface at normal mammalian blood temperature.

7. The method of claim 6, wherein DPPC and PG are present in a weight ratio of from about 6:4 to 8:2.

8. The method of claim 1, wherein at least one component of the SAPL comprises a D or DL mixture.

9. A dispersion device for administering a medicament useful in the treatment of asthma which comprises a sterile cartridge containing essentially animal protein free finely-divided particles of a blend of DPPC and PG, and means for introducing said particles into a gas stream as the patient inhales, said particles including a majority having a size within the range of 0.5 to 2 $\mu$m.

10. The dispersion device of claim 9, wherein the DPPC and the PG are present in a weight ratio of from about 9:1 to 1:9.

11. The device of claim 9, further comprising a source of propellant to form the gas stream.

* * * * *